(12) United States Patent
Chewter et al.

(10) Patent No.: US 8,754,280 B2
(45) Date of Patent: *Jun. 17, 2014

(54) METHOD FOR START-UP OF AN OXYGENATE-TO-OLEFIN PROCESS

(75) Inventors: Leslie Andrew Chewter, Amsterdam (NL); Rajaram Ramesh, Amsterdam (NL); Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,308

(22) Filed: Sep. 7, 2012

(65) Prior Publication Data

US 2013/0245294 A1    Sep. 19, 2013

(30) Foreign Application Priority Data

Sep. 7, 2011  (EP) ..................................... 11180340

(51) Int. Cl.
*C07C 1/20*    (2006.01)
(52) U.S. Cl.
USPC ............ 585/640; 549/523; 585/326; 585/638
(58) Field of Classification Search
USPC .......... 549/513, 523; 585/324, 326, 639, 640
See application file for complete search history.

(56) References Cited

U.S. PATENT DOCUMENTS

| 4,567,029 | A | 1/1986 | Wilson et al. | |
| 6,049,017 | A * | 4/2000 | Vora et al. | 585/324 |
| 7,238,846 | B2 * | 7/2007 | Janssen et al. | 585/640 |
| 7,247,764 | B2 * | 7/2007 | Janssen et al. | 585/640 |
| 7,402,718 | B2 * | 7/2008 | Janssen et al. | 585/638 |
| 7,592,496 | B2 * | 9/2009 | Vora et al. | 585/324 |
| 8,049,054 | B2 * | 11/2011 | Chewter et al. | 585/643 |
| 8,269,056 | B2 * | 9/2012 | Van Westrenen et al. | 585/639 |
| 8,507,742 | B2 * | 8/2013 | Chewter et al. | 585/324 |
| 2007/0155999 | A1 | 7/2007 | Pujado et al. | |
| 2007/0203380 | A1 | 8/2007 | Vora et al. | |

FOREIGN PATENT DOCUMENTS

| WO | 2006020083 | 2/2006 |
| WO | 2007135049 | 11/2007 |
| WO | 2008147543 | 12/2008 |

* cited by examiner

*Primary Examiner* — Golam M M Shameem

(57) ABSTRACT

The present invention provides a method for start-up of an Oxygenate-to-Olefins process, which process comprises the steps:

a) providing an oxygenate-comprising feedstock to an Oxygenate-to-Olefins reaction zone and contacting the feedstock with a zeolite-comprising catalyst at a temperature in the range of from 450 to 700° C. ° C., to obtain an reaction product containing olefins;

b) separating the reaction product obtained in step a) in at least a product fraction containing ethylene and/or propylene and a product fraction containing C4+ olefins;

c) recycling at least part of the C4+ olefins in the product fraction containing C4+ olefins to the Oxygenate-to-Olefins reaction zone in step (a), characterized in that upon start-up the oxygenate-comprising feedstock initially comprises a first amount of externally supplied tert-alkyl ether and subsequently the amount of externally supplied tert-alkyl ether in the oxygenate-comprising feedstock is reduced.

15 Claims, No Drawings

METHOD FOR START-UP OF AN OXYGENATE-TO-OLEFIN PROCESS

This application claims the benefit of European Application No. 11180340.9 filed Sep. 7, 2011, which is incorporated herein by reference.

FIELD OF THE INVENTION

The invention relates to a method for start-up of an Oxygenate-to-Olefins process.

BACKGROUND TO THE INVENTION

Conventionally, ethylene and propylene are produced via steam cracking of paraffinic feedstocks including ethane, propane, naphtha and hydrowax. An alternative route to ethylene and propylene is an oxygenate-to-olefin (OTO) process. Interest in OTO processes for producing ethylene and propylene is growing in view of the increasing availability of natural gas. Methane in the natural gas can be converted into for instance to methanol or dimethylether (DME), both of which are suitable feedstocks for an OTO process.

In EP2018359 A1, an OTO process is described wherein an oxygenate such as methanol or DME is provided with an C4+ olefinic co-feed to a reaction zone together comprising a suitable zeolite conversion catalyst and converted to ethylene and propylene. During start-up of the process of EP2018359 A1, an external C4+ olefinic co-feed is supplied to the process to provide the C4+ olefinic co-feed required for the reaction. At a certain stage the external olefinic co-feed is at least partially replaced by recycling C4+ olefins obtained from the effluent of the reaction zone and the process moves in to a steady state or normal operation.

The use of a feedstock comprising oxygenates together with an olefin co-feed is typical for OTO process that use a zeolite-comprising catalyst. During start-up of the process, no reaction product is yet produced and therefore external source of olefins needs to be provided. Typically, this is a C4 hydrocarbon fraction obtained from for instance a steam cracker or a catalytic cracker. As the process operation moves from the start-up phase into normal operation, sufficient reaction product is produced and the supply of external olefins is gradually reduced, while the recycle of olefins, in particular C4 olefins, from the reaction product to the OTO zone is increased to satisfy the olefin demand of the OTO process.

A disadvantage of using an external source of olefins as described herein above is that these external olefins are only required during start up of the process. For instance at a refinery site, this would require rerouting of olefin-comprising hydrocarbon fractions away from their designated purpose. Not only does this present logistic challenges, it may also cause disruption of processes that normally rely on these olefin-comprising hydrocarbon fractions as feedstock. Typically, an external source of olefins contains diolefins. These diolefins can cause additional coke formation during start-up. During normal operation of the process, these diolefins are typically removed by a selective hydrogenation unit. However, these units are generally not yet operational during start-up. By using a tert-alkyl ether during start-up, instead of the external source of olefins, no diolefins are present. An additional disadvantage is that these olefin comprising hydrocarbon fractions typically comprise significant concentrations of paraffins. Paraffins do not react in the OTO process, and therefore only act as a diluent. Although this may be acceptable during normal operation it is undesired during start-up.

There is a need in the art for a more efficient method to conduct the start-up of such an OTO process.

SUMMARY OF THE INVENTION

It has now been found that by replacing the external olefins, provided to the process during start-up, by a tert-alkyl ether, a more efficient method for starting up an OTO process is obtained.

Accordingly the present invention provides a method for start-up of an Oxygenate-to-Olefins process, which process comprises the steps:

a) providing an oxygenate-comprising feedstock to an Oxygenate-to-Olefins reaction zone and contacting the feedstock with a zeolite-comprising catalyst at a temperature in the range of from 450 to 700° C. ° C., to obtain an reaction product containing olefins;

b) separating the reaction product obtained in step a) in at least a product fraction containing ethylene and/or propylene and a product fraction containing C4+ olefins;

c) recycling at least part of the olefins in the product fraction containing olefins C4+ to the Oxygenate-to-Olefins reaction zone in step (a), characterised in that upon start-up the oxygenate comprising feedstock initially comprises a first amount of externally supplied tert-alkyl ether and subsequently the amount of externally supplied tert-alkyl ether in the oxygenate-comprising feedstock is reduced.

In the method for starting-up an OTO process according to the present invention, the external olefins provided in the prior art during start-up are replaced by tert-alkyl ethers. Reference herein to a tert-alkyl ether is to an ether of an iso-olefin and an alkyl alcohol. These tert-alkyl ethers have the advantage in that these combine an iso-olefin and an alcohol into one molecule. These tert-alkyl ethers are readily mixable with typical oxygenate feedstocks such as methanol and dimethyl ether and may conveniently be combined with methanol or dimethyl ether to form the oxygenate-comprising feedstock. Contrary to a typical C4 hydrocarbon fraction, the selected tert-alkyl ethers have properties, such as density and boiling temperatures, comparable to methanol allowing the use of systems, designed for preheating and vaporisation of methanol-based oxygenate feedstocks, for tert-alkyl ethers-comprising feedstocks with little or no adaptation. As a result only limited means need to be provided to be provided to supply the tert-alkyl ethers to the process during start-up.

The tert-alkyl ethers, in particular methyl tert-butyl ether (MTBE) and tert-amyl-methyl ether (TAME), are readily available on the market and therefore do not require rerouting of feedstocks. The tert-alkyl ethers typically do not contain paraffins and even in its crude form typically comprise predominantly the tert-alkyl ether and the alcohol used to form the tert-alkyl ether, both of which are suitable reactants during start up of the OTO process. The tert-alkyl ethers are liquids at ambient conditions and can therefore be stored without the need to provide cooled or pressurised storage facilities Although, tert-alkyl ethers have boiling temperatures similar to that of for instance methanol, the heat of evaporation for tert-alkyl ethers is significantly lower compared to for instance methanol. For example, the heat of evaporation for MTBE is approximately 320 kJ/kg, whereas the heat of evaporation for methanol is approximately 1178 kJ/kg. Consequently, significantly less energy is required to vaporise the tert-alkyl ethers compared to methanol. By replacing at least part of a methanol feed to an existing OTO process by MTBE, more feedstock can be evaporated in the feed vaporiser for the same energy consumption, or the same amount of feedstock can be vaporised at a lower energy consumption. This again is beneficial during the start-up of the process, in particular in the absence of hot effluent streams available for heat exchange.

DETAILED DESCRIPTION OF THE INVENTION

Ethylene and propylene can be produced from an oxygenate-comprising feedstock, in particular comprising methanol or dimethyl ether (DME), by contacting the oxygenate-comprising feedstock with a zeolite-comprising catalyst at elevated temperatures in a reaction zone. These processes are referred to as oxygenate-to-olefin (OTO) processes. The reaction product of such an OTO process typically comprises the desired product fraction containing ethylene and/or propylene, but also comprises a product fraction containing C4+ olefins. Preferably, the reaction product comprises advantageously at least 50 mol %, in particular at least 50 wt %, ethylene and propylene, based on total hydrocarbon content in the reaction product.

The reaction product is separated into at least product fraction containing ethylene and/or propylene and a product fraction containing C4+ olefins. The product fraction containing C4+ olefins contains C4+ olefins, both iso-olefins and normal olefins, but will also contain paraffins. The product fraction containing C4+ olefin is herein also referred to as C4+ product fraction. The reaction product may be separated using any suitable work-up section. The design of the work-up section depends on the exact composition of the reaction product stream, and may include several separation steps.

Part of these C4+ olefins are recycled back to the reaction zone. In the reaction zone, at least part of the recycled olefins react with the oxygenate to form at least ethylene and/or propylene.

The present invention provides a method for start-up of such an OTO process. Upon start-up of the OTO process no reaction product is yet produced and therefore no C4+ olefins obtained from such reaction product can be recycled to the reaction zone. Therefore, upon start-up initially another reactant must be provided to the process to replace the C4+ olefins until sufficient C4+ olefins are produced as part of a reaction product.

In the method according to the present invention it is prescribed that upon start-up the oxygenate-comprising feedstock initially comprises a first amount of externally supplied tert-alkyl ether. The term "initially" herein refers to the period starting as the oxygenate-comprising feedstock is provided to the reaction zone for the first time. Subsequent to the initial period, i.e. as soon as oxygenate-comprising feedstock containing the externally supplied tert-alkyl ether is provided to the reaction zone and sufficient reaction product is obtained to separate out a C4+ product fraction, C4+ olefins become available for the OTO reaction and the amount of externally supplied tert-alkyl ether in the oxygenate-comprising feedstock may be reduced.

The initial oxygenate-comprising feedstock, i.e. oxygenate-comprising feedstock containing the externally supplied tert-alkyl ether may be contacted with the catalyst under the same reaction conditions used for OTO process during normal operation.

In the method according to the present invention, an oxygenate-comprising feedstock is initially provided upon start-up. The oxygenate-comprising feedstock comprises at least one tert-alkyl ether, preferably selected from the group of methyl tert-butyl ether (MTBE), ethyl tert-butyl ether (ETBE), tert-amyl methyl ether (TAME) and tert-amyl ethyl ether (TAEE).

The oxygenate-comprising feedstock may be a feedstock comprising oxygenates selected from the group consisting of MTBE, ETBE, TAME and TAEE. However, preferably, the oxygenate-comprising feedstock further comprises other oxygenates in particular methanol and/or DME and preferably methanol. More preferably, the oxygenate-comprising feedstock initially consists of components selected from the group of externally supplied tert-alkyl ether, methanol, dimethyl ether and diluent, even more preferably selected from the group of tert-alkyl ether, methanol and steam. Steam is one suitable diluent, other suitable diluents include nitrogen, argon and methane. Reference hereinto a diluent is to a non-reactive diluent.

The oxygenate-comprising feedstock may comprise any amount of tert-alkyl ether, desired, preferably in the range of from 3 to 50 wt % of tert-alkyl ether, based on the weight of the oxygenates in the oxygenate-comprising feedstock, more preferably in the range of from 5 to 40 wt %.

With respect to the tert-alkyl ethers it is believed, without wishing to be bound to a particular theory, that upon contacting the zeolite-catalyst, the tert-alkyl ether decomposes into its corresponding alcohol, i.e. methanol or ethanol, and iso-olefin, i.e. isobutene or isopentene. This decomposition reaction is acid-catalysed. Zeolite are acidic by nature. In the absence of sufficiently acid groups in the zeolite-comprising catalyst it may be preferred to add such groups either by treating the zeolite-comprising catalyst to introduce such groups essentially at the surface of the catalyst through impregnation with an acid that resides on the catalyst after calcination, for instance by treating the zeolite-comprising catalyst with an acid, such as phosphoric acid, or adding an acid component to catalyst formulation comprising the molecular sieve-comprising catalyst, such as alumina.

Alternatively, the oxygenate-comprising feedstock is contacted with an acid catalyst, prior to contacting the molecular sieve-comprising catalyst. This may for instance be done by passing oxygenate-comprising feedstock through an acid catalyst comprising bed or by passing the feedstock through an acid grid or filter. Preferably, the oxygenate-comprising feedstock is contacted with the acid catalyst at a temperature above 150° C. More preferably, the oxygenate-comprising feedstock is contacted with the acid catalyst at a temperature above 350° C.

Preferably, steam is present as the tert-alkyl ether contacts the catalyst. Steam is believed to increase the selectivity of tert-alkyl ether decomposition reaction.

The alcohol and olefin obtained are subsequently converted to form the reaction product. Notwithstanding the above, it is not excluded that in contact with the zeolite-comprising catalyst the tert-alkyl ethers are converted directly to the reaction product.

As mentioned above, in the method according the present invention, subsequent to the initial period the amount of externally supplied tert-alkyl ether in the oxygenate-comprising feedstock is lowered as C4+ olefins become available as part of the further product comprising C4+ olefins.

In one embodiment, the method includes that subsequent to the initial period at least part of the first amount of externally supplied tert-alkyl ether is substituted by providing at least part of the C4+ olefins in the C4+ product fraction to the reaction zone. This can be done by recycling part of the C4+ product fraction to the OTO reaction zone. However, a certain part thereof, such as between 1 and 5 wt %, needs to be withdrawn as purge, since otherwise saturated hydrocarbons, in particular C4 saturated hydrocarbons (butane) would build up in the process, which are substantially not converted under the OTO reaction conditions.

In an alternative embodiment of the method, at least part of the first amount of externally supplied tert-alkyl ether is subsequently substituted by a further tert-alkyl ether. This further tert-alkyl ether is obtained by etherification of iso-olefins contained the C4+ product fraction with methanol and/or ethanol, preferably methanol.

The formed ethers can be separated from the remainder of the C4+ product fraction. Only iso-olefins, wherein the double bound is located directly adjacent to a tertiary carbon atom can react with methanol and/or ethanol to form tert-alkyl ethers, such iso-olefins are herein referred to as tertiary iso-olefins. Examples of such tertiary iso-olefins include isobutene, 2-methyl-1-butene and 2-methyl-2-butene. An example of an iso-olefin that is not a tertiary iso-olefin is 3-methyl-1-butene. Therefore, in the process according to the present invention at least part of the iso-olefins in the C4+ product fraction should be tertiary iso-olefins.

The further tert alkyl ethers may be formed by subjecting at least part of the C4+ product fraction comprising C4+ olefins to an etherification process. In the etherification process the C4+ product fraction is contacted with methanol and/or ethanol in the presence of a suitable etherification catalyst. When the iso-olefins in the C4+ product fraction are contacted with methanol and/or ethanol in the presence of an etherification catalyst, at least part of the iso-olefins are converted with methanol and/or ethanol to tert-alkyl ethers. Examples of such tert-alkyl ethers are methyl tert-butyl ether (MTBE), ethyl tert-butyl ether (ETBE), tert-amyl methyl ether (TAME) and tert-amyl ethyl ether (TAEE). These are tert-alkyl ethers of methanol and ethanol with respectively isobutene and isopentene. From the etherification process, an etherification product stream is retrieved. The etherification product stream will comprise the formed tert-alkyl ethers and the remainder of the C4+ product fraction, i.e. the unreacted components. In addition, the etherification product stream may also comprise unreacted methanol and/or ethanol.

At least part, and preferably all, of the etherification product stream is separated into at least an ether-enriched stream and an iso-olefin-depleted C4+ product fraction. The separation of the etherification product stream into an ether-enriched stream and an iso-olefin-depleted C4+ product fraction can be done with normal separation means provided in the art. Typically the etherification reaction is performed in the presence of an excess of alcohol, i.e. above reaction stoichiometry with the iso-olefin. Due to the large difference in boiling temperature between the formed ethers and the remaining components in the etherification product stream, the etherification product stream may be separated using conventional distillation columns and gas/liquid separators. It is preferred to concentrate any methanol in the ether-enriched stream. Due to the relatively high boiling point of methanol and ethanol, the bulk of the excess methanol and ethanol can be directed toward the ether-enriched stream. Alcohols may form an azeotropic mixture with the hydrocarbons in the iso-olefin-depleted C4+ product fraction. It may be desired to remove the alcohol from the iso-olefin-depleted C4+ product fraction. This can be done using a water extraction step, which is well known in the art relating to tert-alkyl production processes.

The etherification process may be any suitable etherification process available in the art for etherifying methanol and iso-olefins to tert-alkyl ethers. Reference is made to the Handbook of MTBE and Other Gasoline Oxygenates, H. Hamid and M. A. Ali ed., 1$^{st}$ edition, Marcel Dekker, New York, 2004, pages 65 to 223, where several established process and catalyst for preparing tert-alkyl ethers such as MTBE and TAME are described. In particular reference is made to chapter 9, pages 203 to 220 of the Handbook of MTBE and Other Gasoline Oxygenates, wherein suitable commercial etherification processes are described. A preferred etherification process is an etherification process wherein the iso-olefins are converted with methanol to a tert-alkyl ether in the presence of a catalyst. Any homogeneous or heterogeneous Brönsted acid may be used to catalyze the etherification reaction. Such catalyst include: sulfuric acid, zeolites, pillared silicates, supported fluorocarbonsulphonic acid polymers and protonated cation-exchange resins catalyst, preferred catalyst are protonated cation-exchange resins catalyst due to the higher catalytic activity and the bound acid sites. A commonly used catalyst is Amberlyst 15.

Preferably, the iso-olefins are converted with methanol and/or ethanol to a tert-alkyl ether at a temperature in the range of from 30 to 100° C., more preferably 40 to 80° C. Preferably, the iso-olefins are converted with methanol and/or ethanol to a tert-alkyl ether at a pressures in the range of from 5 to 25 bar, more preferably 6 to 20 bar.

The iso-olefins may be converted with methanol and/or ethanol to a tert-alkyl ether in any etherification process, however, one preferred etherification process is based on a reactive distillation, which allows for a continuous etherification and separation of the formed ethers.

An advantage of providing iso-olefins obtained from the reaction product to the reaction zone in the form of tert-alkyl ethers is that the transition from the initial oxygenate-comprising feedstock to the oxygenate feedstock with reduced amounts of externally supplied tert-alkyl ethers can be done smoothly, without the need for a significant adaption of the process conditions. In addition, this embodiment reduces the provision of diolefins and paraffins from the reaction product back to the reaction zone.

In the present invention, a method is provided for start-up of an OTO process, wherein an oxygenate-comprising feedstock, initially comprising a first amount of externally supplied tert-alkyl ether, is converted to olefins. This may be any suitable OTO process known in the art. Preferably, it is an OTO process in which an oxygenate feedstock is contacted in an OTO zone with an oxygenate conversion catalyst under oxygenate conversion conditions, to obtain a conversion effluent comprising lower olefins, preferably the conversion effluent comprises advantageously at least 50 mol %, in particular at least 50 wt %, ethylene and propylene, based on total hydrocarbon content in the conversion effluent.

Reference herein to an oxygenate feedstock is to an oxygenate-comprising feedstock. In the OTO zone, at least part of the feedstock is converted into a product containing one or more olefins, preferably including lower olefins, in particular ethylene and typically propylene.

The oxygenate used in the OTO process according to the invention is preferably an oxygenate which comprises at least one oxygen-bonded alkyl group. Examples of oxygenates that can be used in the oxygenate feedstock include alcohols and ethers. Examples of preferred oxygenates include alcohols, such as methanol, ethanol, propanol; and dialkyl ethers, such as dimethylether, diethylether, methylethylether. Preferably, the oxygenate is methanol or dimethylether, or a mixture thereof.

Preferably the oxygenate feedstock comprises at least 50 wt % of oxygenate, in particular methanol and/or dimethylether, based on the total of hydrocarbons and oxygenates in the oxygenate feedstock, more preferably at least 70 wt %.

The oxygenate feedstock can comprise an amount of diluents. During the conversion of the oxygenates, steam is produced as a by-product, which serves as an in-situ produced diluent. Optionally additional steam is added as diluent. The amount of additional diluent that needs to be added depends on the in-situ water make, which in turn depends on the composition of the oxygenate-comprising feed. Where methanol produces 1 mol of water per mol of carbon atoms supplied to the process, MTBE, for example only produces 0.20 mol of water per 1 mol of carbon atoms supplied to the process. Where the diluent is water or steam, the molar ratio of oxygenate to diluent is between 10:1 and 1:20. In case, the oxygenate-comprising feedstock comprises in the range of from 0.01 to 50 wt %, preferably of from 1 to 10 wt %, of tert-alkyl ether, based on the oxygenates in the oxygenate-comprising feedstock, the molar ratio of oxygenate to diluent is preferably in the range of from 3:1 to 1:5, preferably 2:1 to 1:2. In case, the oxygenate-comprising feedstock comprises in the range of from 50 to 100 wt %, preferably 60 to 95 wt %, of tert-alkyl ether, based on the oxygenates in the oxygenate-comprising feedstock, the molar ratio of oxygenate to diluent is preferably in the range of from 1:3 to 1:15, preferably 1:4 to 1:10.

Due to the low in-situ water make of tert-alkyl ethers, the use of diluents other than water may be preferred, in particular when the catalyst is sensitive to hydrothermal deactivation. Other suitable diluents include inert gases such as nitrogen, but may also include paraffins.

Preferably, in addition to the oxygenate, an olefinic co-feed is provided along with and/or as part of the oxygenate feedstock to the OTO process. Reference herein to an olefinic co-feed is to an olefin-comprising co-feed. The olefinic co-feed preferably comprises C4 and higher olefins, more preferably C4 and C5 olefins. Preferably, the olefinic co-feed comprises at least 25 wt %, more preferably at least 50 wt %, of C4 olefins, and at least a total of 70 wt % of C4 hydrocarbon species.

Preferably, at least 70 wt % of the olefinic co-feed, during normal operation, is formed by a recycle stream of a C3+ or C4+ hydrocarbon fraction from the OTO conversion effluent, preferably at least 90 wt % of olefinic co-feed, based on the whole olefinic co-feed, is formed by such recycle stream. This can be done by recycling at least part of the C4+ hydrocarbon fraction, preferably C4-C5 hydrocarbon fraction, more preferably C4 hydrocarbon fraction, in the OTO effluent.

The preferred molar ratio of oxygenate in the oxygenate feedstock to olefin in the olefinic co-feed provided to the OTO conversion zone depends on the specific oxygenate used and the number of reactive oxygen-bonded alkyl groups therein. Preferably the molar ratio of oxygenate to olefin in the total feed, i.e. oxygenate feedstock, and olefinic co-feed, lies in the range of 20:1 to 1:10, more preferably in the range of 18:1 to 1:5, still more preferably in the range of 15:1 to 1:3, even still more preferably in the range of 12:1 to 1:3. For purposes of calculating the molar ratio of oxygenate to olefin in the total feed, the olefins provided to the process as part of the tert-alkyl ether must also be taken into account.

A variety of OTO processes is known for converting oxygenates such as for instance methanol or dimethylether to an olefin-containing product, as already referred to above. One such process is described in WO A 2006/020083. Processes integrating the production of oxygenates from synthesis gas and their conversion to light olefins are described in US20070203380A1 and US20070155999A1.

In the OTO process according to the present invention zeolite-comprising catalyst is used. Such catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Zeolites have a molecular framework of one, preferably two or more corner-sharing [TO4] tetrahedral units, more preferably, two or more [SiO4] and [AlO4] tetrahedral units. These silicon and aluminum based zeolites are among other metal containing silicon, aluminum and/or phosphorous based molecular sieves described in detail in numerous publications including for example, U.S. Pat. No. 4,567,029. In a preferred embodiment, the zeolites have 8-, 10- or 12-ring structures and an average pore size in the range of from about 3 Å to 15 Å.

Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Zeolites are preferred when the feedstock to be converted comprises olefins, e.g. in step (a).

Particular preferred zeolite-comprising catalysts are catalysts comprising at least one zeolite selected from MFI, MEL, TON and MTT type zeolites, more preferably at least one of ZSM-5, ZSM-11, ZSM-22 and ZSM-23 zeolites.

Preferred catalysts comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80. The oxygenate conversion catalyst can comprise at least 1 wt %, based on total molecular sieve in the oxygenate conversion catalyst, of the second molecular sieve having more-dimensional channels, preferably at least 5 wt %, more preferably at least 8 wt %.

Particular preferred catalyst include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50% wt of such zeolites, based on total zeolites in the catalyst.

A particularly preferred catalyst comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11. Such further zeolite can have a beneficial effect on the stability of the catalyst in the course of the process and under hydrothermal conditions.

The catalyst may comprise phosphorous as such or in a compound, i.e. phosphorous other than any phosphorous included in the framework of the molecular sieve. It is preferred that an MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, a catalyst comprising MEL or MFI-type zeolites comprises phosphorous as such or in a compound in an elemental amount of from 0.05-10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

It is preferred that zeolites and respectively molecular sieves in the hydrogen form are used in the catalyst for both step (a) and (f), e.g., HZSM-22, HZSM-23, and HZSM-48, HZSM-5. Preferably at least 50 wt %, more preferably at least 90 wt %, still more preferably at least 95 wt % and most preferably 100 wt % of the total amount of molecular sieve used is in the hydrogen form. It is well known in the art how to produce such molecular sieves in the hydrogen form.

Preferably, the oxygenate-comprising feedstock is preheated to a temperature in the range of from 200 to 550° C., preferably 350 to 500° C. prior to contacting with the zeolite-comprising catalyst.

The reaction conditions of the oxygenate conversion include a reaction temperature of 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Typically the catalyst deactivates in the course of the process, primarily due to deposition of coke on the catalyst. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 μm, preferably 50-100 μm.

The process may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

Where the reaction product comprises ethylene, least part of the ethylene may be further converted into at least one of polyethylene, mono-ethylene-glycol, ethylbenzene and styrene monomer. Where the reaction product comprises propylene, at least part of the propylene may be further converted into at least one of polypropylene and propylene oxide.

EXAMPLES

The invention is illustrated by the following non-limiting examples.

Example 1

Several molecular sieves were tested to show their ability to convert MTBE to an olefinic product. To test the molecular sieves for catalytic performance, a powder of the respective molecular sieves was pressed into tablets and the tablets were broken into pieces and sieved. MTBE was reacted over the catalysts which were tested to determine their selectivity towards olefins, mainly ethylene and propylene from oxygenates. For the catalytic testing, the sieve fraction of 40-80 mesh was used. Prior to reaction, the molecular sieves were treated ex-situ in air at 550° C. for 2 hours.

The reaction was performed using a quartz reactor tube of 1.8 mm internal diameter. The molecular sieve samples were heated in nitrogen to the reaction temperature and a mixture consisting of 6 vol % MTBE balanced in $N_2$ was passed over the catalyst at atmospheric pressure (1 bar). The Gas Hourly Space Velocity (GHSV) is determined by the total gas flow over the zeolite weight per unit time (ml.gzeolite$^{-1}$.h$^{-1}$). The gas hourly space velocity used in the experiments was 10000 (ml.gzeolite$^{-1}$.h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The effluent from the reactor obtained at several reactor temperatures was analyzed. The results are shown in Table 1.

TABLE 1

| T [° C.] | Catalyst | C2= [wt %] | C3= [wt %] | C4= [wt %] | C5 [wt %] | Light ends [wt %] | C6+ [wt %] | C4 paraffin [wt %] |
|---|---|---|---|---|---|---|---|---|
| 420 | SAPO-34* | 7.90 | 15.15 | 65.43 | 9.18 | 0.19 | 1.06 | 1.09 |
| 420 | ZSM-5# | 10.86 | 28.10 | 15.93 | 8.13 | 0.12 | 23.56 | 13.31 |
| 525 | ZSM-5# | 26.77 | 38.11 | 11.46 | 2.69 | 0.03 | 13.01 | 7.92 |
| 525 | ZSM-5## | 17.89 | 39.85 | 25.49 | 3.22 | 1.79 | 9.69 | 2.07 |
| 525 | ZSM-23 | 20.73 | 42.89 | 29.00 | 2.05 | 0.59 | 3.62 | 1.12 |
| 525 | ZSM-22 | 17.19 | 39.88 | 35.52 | 2.12 | 0.44 | 3.99 | 0.86 |

*Not according to the invention
SAR 80
SAR 280

For all tested catalyst, the conversion of MTBE was complete. No MTBE or methanol was detected in the effluent of the reactor.

The zeolite catalysts, i.e. ZSM-5, ZSM-22 and ZSM-23, show a good conversion of the MTBE, including the isobutene part of the MTBE, to ethylene and propylene. An advantage of the one-dimensional zeolites having 10-membered ring channels, i.e. ZSM-22 and ZSM-23, is the lower paraffin make and C6+ make compared to the multi-dimensional ZSMS zeolites.

By reducing the SAR of the ZSM-5 catalyst, the ethylene and propylene yield is improved, while significantly less C4 olefins are produced.

The non-zeolite SAPO-34 catalyst shows little conversion iso-C4 olefins as can be seen from the high C4 olefin content in the effluent of the reactor. It will be clear from table 1, that zeolite catalyst show a better conversion of C4 olefins to the desired ethylene and propylene products.

Increasing the reaction temperature, results in a reduction of the C4 olefin content in the effluent of the reaction.

Example 2

Several zeolites were tested to show their ability to convert a mixture of MTBE and methanol to an olefinic product. To test the zeolites for catalytic performance, a powder of the respective zeolites was pressed into tablets and the tablets were broken into pieces and sieved. A mixture of MTBE and methanol was reacted over the catalysts which were tested to determine their selectivity towards olefins, mainly ethylene and propylene from oxygenates. For the catalytic testing, the sieve fraction of 40-80 mesh was used. Prior to reaction, the zeolites were treated ex-situ in air at 550° C. for 2 hours.

The reaction was performed using a quartz reactor tube of 1.8 mm internal diameter. The zeolite samples were heated in nitrogen to 525° C. and a mixture consisting of 3 vol % MTBE and 3 vol % methanol, balanced in $N_2$ was passed over the catalyst at atmospheric pressure (1 bar). The Gas Hourly Space Velocity (GHSV) is determined by the total gas flow over the zeolite weight per unit time (ml.gzeolite$^{-1}$.h$^{-1}$). The gas hourly space velocity used in the experiments was 10000 (ml.gzeolite$^{-1}$.h$^{-1}$). The effluent from the reactor was analyzed by gas chromatography (GC) to determine the product composition. The composition has been calculated on a weight basis of all hydrocarbons analyzed. The composition has been defined by the division of the mass of a specific product by the sum of the masses of all products. The results are shown in Table 2.

TABLE 2

| T [° C.] | Catalyst | C2= [wt %] | C3= [wt %] | C4= [wt %] | C5 [wt %] | Light ends [wt %] | C6+ [wt %] | C4 paraffin [wt %] |
| --- | --- | --- | --- | --- | --- | --- | --- | --- |
| 525 | ZSM-5# | 25.72 | 37.64 | 11.57 | 3.24 | 0.65 | 13.79 | 7.41 |
| 525 | ZSM-5## | 17.66 | 42.42 | 20.31 | 3.31 | 1.82 | 12.88 | 1.61 |
| 525 | ZSM-23 | 21.45 | 46.66 | 21.09 | 2.77 | 0.81 | 6.16 | 1.06 |
| 525 | ZSM-22 | 17.84 | 48.46 | 24.30 | 2.61 | 0.83 | 5.24 | 0.71 |

SAR 80
SAR 280

The zeolite catalysts do not show a significant change in the obtained C2 to C4 olefinic product slate, when methanol is added to the MTBE feed. As a result, it can be expected that for an existing methanol based OTO process using a zeolite catalyst, MTBE can be blended into the methanol feed without requiring significant changes to the process operation.

What is claimed is:

1. A method for start-up of an Oxygenate-to-Olefins process in which C4+ olefins are recycled, which process comprises the steps:
   a) providing an oxygenate-comprising feedstock to an Oxygenate-to-Olefins reaction zone and contacting the feedstock with a zeolite-comprising catalyst at a temperature in the range of from 450 to 700° C., to obtain an reaction product containing olefins;
   b) separating the reaction product obtained in step a) into at least a product fraction containing ethylene and/or propylene and a product fraction containing C4+ olefins;
   c) recycling at least part of the C4+ olefins in the product fraction containing C4+ olefins to the Oxygenate-to-Olefins reaction zone in step (a),
   characterised in that upon start-up the oxygenate-comprising feedstock initially comprises a first amount of externally supplied tert-alkyl ether and subsequently the amount of externally supplied tert-alkyl ether in the oxygenate-comprising feedstock is reduced as C4+ olefins become available from step (c) and are recycled.

2. A method according to claim 1, wherein the oxygenate-comprising feedstock initially consists of components selected from the group of externally supplied tert-alkyl ether, methanol, dimethyl ether and diluent.

3. A method according to claim 1, wherein the oxygenate-comprising feedstock initially consists of components selected from the group of externally supplied tert-alkyl ether, methanol and steam.

4. A method according to claim 1, wherein the oxygenate-comprising feedstock initially contains in the range of from 3 to 50 wt % of tert-alkyl ether based on the oxygenates in the oxygenate-comprising feedstock.

5. A method according to claim 1, wherein subsequently at least part of the first amount of externally supplied tert-alkyl ether is substituted by at least part of the C4+ olefins in the product fraction containing C4+ olefins.

6. A method according to claim 1, wherein subsequently at least part of the first amount of externally supplied tert-alkyl ether is substituted by a further tert-alkyl ether obtained by etherification of iso-olefins contained the product fraction containing C4+ olefins with methanol and/or ethanol.

7. A method according to claim 6, wherein the iso-olefins contained in the product fraction containing C4+ olefins include at least one of isobutene and isopentene.

8. A method according to claim 6, wherein the iso-olefins are converted with methanol to the tert-alkyl ether by contacting the iso-olefin with methanol in the presence of an etherification catalyst at a temperature in the range of from 30 to 100° C.

9. A method according to claim 7, wherein the iso-olefins are converted with methanol to the tert-alkyl ether by contacting the iso-olefin with methanol in the presence of an etherification catalyst at a temperature in the range of from 30 to 100° C.

10. A method according to claim 8, wherein the etherification catalyst is a protonated cation-exchange resin catalyst.

11. A method according to claim 9, wherein the etherification catalyst is a protonated cation-exchange resin catalyst.

12. A method according to claim 1, wherein the first amount of externally supplied tert-alkyl contains at least one of methyl tert-butyl ether, ethyl tert-butyl ether, tert-amyl methyl ether and tert-amyl ethyl.

13. A method according to claim 1, wherein the zeolite-comprising catalyst comprises at least one zeolite selected from MFI, MEL, TON and MTT type zeolites.

14. A method according to claim 1, wherein the reaction product comprises ethylene and at least part of the ethylene is further converted into at least one of polyethylene, mono-ethylene-glycol, ethylbenzene and styrene monomer.

15. A method according to claim 1, wherein the reaction product comprises propylene and at least part of the propylene is further converted into at least one of polypropylene and propylene oxide.

* * * * *